United States Patent
Millington et al.

(10) Patent No.: US 9,261,447 B2
(45) Date of Patent: Feb. 16, 2016

(54) APPARATUS AND METHOD FOR MONITORING PARTICLES IN A STACK

(75) Inventors: Roger Bradley Millington, Cambridgshire (GB); David Christopher Unitt, Cambridgshire (GB)

(73) Assignee: PCME Limited, St. Ives, Cambridgshire (GB)

( * ) Notice: Subject to any disclaimer, the term of this patent is extended or adjusted under 35 U.S.C. 154(b) by 552 days.

(21) Appl. No.: 13/582,864

(22) PCT Filed: Mar. 7, 2011

(86) PCT No.: PCT/GB2011/050445
§ 371 (c)(1),
(2), (4) Date: Sep. 5, 2012

(87) PCT Pub. No.: WO2011/107809
PCT Pub. Date: Sep. 9, 2011

(65) Prior Publication Data
US 2013/0044216 A1    Feb. 21, 2013

(30) Foreign Application Priority Data
Mar. 5, 2010 (GB) .................................. 1003704.2

(51) Int. Cl.
*G01N 15/02* (2006.01)
*G01N 21/53* (2006.01)
*G01N 15/00* (2006.01)
*G01N 15/06* (2006.01)
*G01N 21/47* (2006.01)

(52) U.S. Cl.
CPC ............ *G01N 15/0211* (2013.01); *G01N 21/53* (2013.01); *G01N 2015/0046* (2013.01); *G01N 2015/0693* (2013.01); *G01N 2021/4704* (2013.01)

(58) Field of Classification Search
CPC ......... H04N 7/183; H04N 7/18; H04N 7/188; H04N 7/181; F21Y 2101/02; F21Y 2105/008
USPC ...................... 348/143; 356/336–343, 364, 73
IPC .......................................................... H04N 7/18
See application file for complete search history.

(56) References Cited

U.S. PATENT DOCUMENTS

| 4,015,135 A | 3/1977 | Tipton, Jr. |
| 5,305,073 A | 4/1994 | Ford, Jr. |

(Continued)

FOREIGN PATENT DOCUMENTS

| EP | 0586146 | 3/1994 |
| GB | 1368301 | 9/1974 |

(Continued)

OTHER PUBLICATIONS

UK Intellectual Property Office, "Great Britain Search Report", "from Foreign Counterpart of U.S. Appl. No. 13/582,864", Mar. 31, 2010, pp. 1-3, Published in: GB.

(Continued)

*Primary Examiner* — Trang U Tran
(74) *Attorney, Agent, or Firm* — Fogg & Powers LLC

(57) ABSTRACT

A method of monitoring particles in a stack comprises generating on a first side of the stack a beam of light directed towards a second, opposite, side of the stack. The beam is reflected back towards the first side of the stack and through the particles in the stack. An image is obtained of light scattered from the particles. The image is obtained using an imager positioned and oriented to have a field of view that includes unwanted scattered light. The method includes the step of blocking the unwanted scattered light from the image.

22 Claims, 3 Drawing Sheets

(56) References Cited

U.S. PATENT DOCUMENTS

| | | | |
|---|---|---|---|
| 5,438,408 A | 8/1995 | Weichert et al. | |
| 5,748,311 A | 5/1998 | Hamann et al. | |
| 6,677,573 B1 * | 1/2004 | Nakata et al. | 250/216 |
| 7,123,363 B2 * | 10/2006 | Puttappa et al. | 356/450 |
| 2007/0064980 A1 | 3/2007 | Knox et al. | |
| 2007/0222986 A1 | 9/2007 | Palumbo | |

FOREIGN PATENT DOCUMENTS

| | | |
|---|---|---|
| JP | 61051542 | 3/1986 |
| JP | 1018043 | 1/1989 |
| JP | 6123694 | 5/1994 |
| JP | 2007533966 | 11/2007 |
| WO | 9802731 | 1/1998 |
| WO | 2004102498 | 11/2004 |

OTHER PUBLICATIONS

International Preliminary Examining Authority, "International Preliminary Report on Patentability", "from Foreign Counterpart of U.S. Pat. No. 5,748,311", Sep. 20, 2012, pp. 1-12, Published in: WO.

International Searching Authority, "International Search Report and Written Opinion", Dec. 23, 2011, pp. 1-16, Published in: WO.

* cited by examiner

APPARATUS AND METHOD FOR MONITORING PARTICLES IN A STACK

FIELD OF THE INVENTION

The present invention concerns an apparatus and method for monitoring particles in a stack. More particularly, the invention concerns an apparatus and method for monitoring particles in a stack by using a light source.

The term "stack" as used herein refers to a volume through which a gas can pass, for example a chimney, tube, flue, duct or the like.

BACKGROUND OF THE INVENTION

Prior-art methods of monitoring particles in a stack include both electrical and optical methods. In a typical optical method, a beam of light from a laser source is directed across the stack (which is typically of diameter 0.5 m to 10 m). Particles in the stack scatter the laser beam over all solid angles with an angle-dependent intensity typically enhanced in a direction of scatter around the forward direction of an incident beam. A portion of the scattered light is collected by a simple telescope and focused onto a photo-detector; the portion of light collected varies in different prior-art devices (e.g. because the collected light is from different scattering directions).

In addition to the light scattered from particles flowing in the stack, other objects that are illuminated by the laser will scatter light. Objects that provide such unwanted scatter are usually part of the stack or equipment fitted to the stack, including the monitoring equipment itself (which includes windows, mirrors, beam dumps, and lenses). Light scattered from such objects can be misinterpreted by the monitoring apparatus if the light finds its way onto the detector.

Manufacturers of monitoring apparatus go to some trouble to prevent such stray light from reaching the detector. One example prior-art method of elimination of stray light is to restrict the field of view of the telescope so that the detector does not "see" any bright scatter from the laser window or that part of the laser beam which coincides with a stack wall. That method of exclusion necessitates collection of scattered light which is angularly-separated from the forward direction of propagation of the laser beam and is therefore not optimal in terms of intensity and relative immunity from the effect of particle size distribution. Another example prior-art method is to take images of scattered light from particulate matter illuminated at an angle which is far from the optimum angle. Imaging a scatter field at large scatter angles has the advantage of achieving focus and range resolution over the entire field, but that is achieved at the expense of signal strength, and prevents mounting of transmitter and receivers in convenient cross-diametric stack locations.

The present invention seeks to mitigate the above-mentioned problems.

SUMMARY OF THE INVENTION

The present invention provides, according to a first aspect, a method of monitoring particles in a stack, the method comprising:

generating on a first side of the stack a beam of light directed through the particles; and obtaining an image of light scattered from the particles by using an imager including a collecting lens through which the light scattered from the particles passes;

characterised in that unwanted scattered light also passes through the collecting lens, and in that the method includes the step of blocking from the image the unwanted scattered light that has passed through the collecting lens.

Thus, although the image is obtained using an imager having a field of view that includes unwanted scattered light, the method includes the step of removing the effects of one or more spatially separated sources of unwanted scattered light from the image; the removal may be either direct (e.g. by physically blocking the unwanted scattered light) or in preferred embodiments of the invention, after processing and/or analysis of the image. By allowing the imager to have a field of view that includes unwanted scattered light (in contrast to prior-art apparatus, which have their imager positioned and oriented to avoid unwanted scattered light) the imager can image the light scattered from the particles in a more forward direction, relative to the direction of the light beam as it reaches the particles, than can prior art apparatus; that can result in a stronger signal in the imager from the scattered light, both because a more forwardly scattered signal will generally be stronger, and because, having removed the unwanted scattered light or its effect on a signal through a detection system, the remaining light or resulting signal can be considered as being substantially due to scatter by particles in the illuminated part of the field of view. Thus, in one method of analysing the image or set of data to get a single data point from the ensemble of pixelated signals, integrating the signal over the whole image field provides a signal to noise ratio which is higher than that obtained if the effects of unwanted light are not filtered, and thus contribute to the noise.

Example embodiments of the invention thus have improved scatter signal intensity for low levels of dust, compared with prior-art detectors, whilst avoiding or ameliorating the detrimental effects of light scattered directly from the optical components and stack walls which are in the path of the laser beam.

The light scattered from the particles and passing through the collecting lens may have been scattered in a direction that forms an angle of less than 30 degrees from the direction of the light beam as it passes through the particles. Preferably, that angle is less than 20 degrees, less than 15 degrees, less than 10 degrees, less than 5 degrees, or even less than 1 degree.

Imaging the whole field of scatter enables an improved dust scatter signal to be obtained. The method is achieved by masking or filtering off the unwanted light. The field of illumination of the particles by the light is not necessarily over the whole imaged field or even over the majority of the stack area.

The beam of light may be generated on the first side of the stack and directed towards a second, opposite, side of the stack, and the method may further include the step of reflecting the beam back towards the first side of the stack and through the particles in the stack.

The beam of light may be directed obliquely through the particles, so that different areas of the imager receive light scattered from particles at different ranges across the stack. The method may include the step of identifying the range from which each pixel of the imager detects scatter. The range at which each pixel of the imager detects scatter may be used to calibrate the intensity measured at each pixel of the imager and thereby to calculate the distribution of particles across the stack. It may be that a range-resolved set of data points is obtained from the image by integrating over each row or each column of pixels in the imager to generate a single data point for each row or each column. Thus, in another example method of analysing the image or set of data, a single data point is generated by, for example, integrating over only each row or over only each column of a matrix of data from the imager, so that a range-resolved set of data points is obtained for each detected image. In such a case, a known size of the actual illuminating beam is used in an algorithm to normalise each range resolved data point to give a number which is representative of the density of particles over the whole stack.

Thus, a range-resolved measurement of particle concentration distribution along an oblique chord of the stack may be provided, for example for process analysis purposes or for the purpose of applying a weighted calibration for an improved calculation of range-resolved or averaged particle concentration. The method may include the step of analysing the image of the scattered light as a function of pixel location on the imager; that enables measurement of particle levels as a function of distance from the instrument. Thus, the pixels of the image may be range-resolved to provide a measurement of how the particle level varies across the stack diameter. The intensity obtained from scattering particles situated at a given range is dependent on the solid angle of scatter subtended at the scatter site by the imaging objective of a specific area of the imager. The imager may be calibrated having regard to the geometrical optics of the imaging set-up, giving each pixel a range from which it detects scatter. A calculation of the range-dependence may be applied to the intensity obtained from each pixel across the imager in order to correct the range-dependent profile or it can be applied in order to permit a range-weighted average over the total range.

The method may include the step of analyzing the image for particle density by summing the intensity of light in the image. The method may include the step of counting spots of light in the image. The method may include the step of identifying morphologically separated shapes for total area calculation. The process of morphological analysis involves making an assumption that the shapes to be detected in an image are of a specific form, for example, a circle, identifying overlapping shapes in an image and making a calculation of the area of each shape, despite the apparent overlap of shapes; adding the areas of calculated shapes gives a total area which is representative of all of the particles in the object plane which scatter light to be imaged on the imager.

The summing, counting or identifying step may be carried out in software on a processor, or in dedicated hardware.

The unwanted scattered light may be blocked using a physical mask that prevents the unwanted scattered light from being imaged by the imager. The unwanted scattered light may be blocked using a physical mask that is tailored spatially to the shape of the unwanted scattered light in order to prevent it from reaching the imager.

The image will have an image space (i.e. the two-dimensional co-ordinate space of the image, plus one or more additional dimensions arising from one or more other parameters, e.g. intensity of light at each co-ordinate). An example of a physical mask is a shaped opaque material which is situated in a Fourier Transform plane of any lens which forms part or whole of the light imaging system of optical elements in the imager. The shape of the mask may be complex and it may correspond spatially to the low spatial frequency pattern from the unwanted scatter formed at the Fourier Transform plane of the lens.

As an alternative to a physical shaped opaque mask, the unwanted scattered light may be blocked from the image by using a virtual mask, that is by filtering signals representing the image and generated by the imager. The virtual mask may be generated in hardware or software; the virtual mask may act on signals from the imager at any place in the analysis train.

In the case of a virtual mask, the mask may be applied by reading out only those pixel elements of the image which do not contain unwanted scattered light.

In the case of a virtual mask, the mask may be applied in the image space or in a parameter space obtained by performing a spatial Fourier Transform on the image (the masked image may then be a deconvolved filtered signal). Alternatively, the virtual mask may for example be applied by obtaining a sequence of the images and performing a Fourier Transform on the sequence of images in the time domain. By performing a Fourier Transform in the time domain, one may separate, on the one hand, features of the time spectrum that result from scattering from particles from, on the other hand, features of the time spectrum that result from unwanted scattering from objects which have unvarying or different velocities from particles moving through the stack. It may be that the images are processed before the Fourier Transform is applied, for example by the summing, counting or identifying steps described above being applied to each image in the sequence. Such an approach may result in a sequence of data points from a sequence of images, and the Fourier Transform may then be performed on the resulting sequence of data points.

In order to correct for background noise in the image (which may for example result from systematic or dark current sources, or from laser light scattered from within the stack other than from the particles) a reference field may be determined. For example, an average intensity in the absence of particles, per pixel of the image, may be obtained, for example by measuring the intensity of each pixel over a period of several frames (i.e. over a sequence of the images) and rejecting outliers attributed to light which is scattered from particles inconsistently over a pre-determined number of successive images. Another approach is to provide a single average intensity value from a masked area of the image through which the light beam does not pass.

The method may include the step of separating, in software, areas of the image containing light scattered from sources other than the particles from areas containing light scattered from the particles.

The method may include the step of separating, in software, areas of the image containing no scattered light from areas containing scattered light. The method may include the step of monitoring, during monitoring of the particles in the stack, one or more areas of the image that is not illuminated by scattered light. That provides a way of checking the zero level of the imager. Advantageously, the monitoring of the area or areas, and hence the checking of the zero level, may be continuous; in contrast, prior-art methods of zero-checking generally involve interrupting the measurement process, e.g. by switching off the monitoring light source. The monitoring of the one or more areas may be carried out by selecting in software data representing the area or areas. The monitoring of the one or more areas may comprise monitoring of stray ambient light to provide a correction to the monitoring of the scattered light in the regions that are illuminated by scattered light; the accuracy of the scatter monitoring may thereby be improved.

The particles may be dust particles.

The present invention provides, according to a second aspect, an apparatus for monitoring particles in a stack, the apparatus comprising:

a light source for generating on a first side of the stack a beam of light directed through the particles in the stack;

an imager for obtaining an image of light scattered from the particles, the imager including a collecting lens for collecting the light scattered from the particles;

characterised in that the apparatus includes a filter arranged to block from the image unwanted scattered light that has passed through the collecting lens into the imager.

The apparatus may include a reflector for mounting on a second, opposite side of the stack and for reflecting the beam back towards the first side of the stack.

The light source and the imager may be housed together in a common housing; thus, when installed, the apparatus may form a double-pass optical system wherein the light source and the imager are housed together on one side of the stack and the reflector is provided at the opposite side of the stack.

The light source may be a laser source and the light beam may thus be a laser beam. The light may be visible light. The laser source may be a solid-state laser, for example a frequency-doubled vanadate laser, which may for example be neodymium-doped.

The reflector may be for example a retroreflector, corner cube, plane mirror, convex mirror or concave mirror.

The apparatus may be arranged so that the imager is positioned between the direction of the light beam emitted from the light source and the direction of the light beam as it is reflected by the reflector.

The image may be formed in the imager by for example a charge-coupled device (CCD) or CMOS detector.

The apparatus may further comprise data processing means for carrying out one or more data processing steps, for example as described above in respect of the first aspect of the invention.

The filter may be a physical mask. The filter may be an electronic or software filter.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present invention will now be described by way of example only with reference to the accompanying schematic drawings of which.

DETAILED DESCRIPTION

Figure 1:
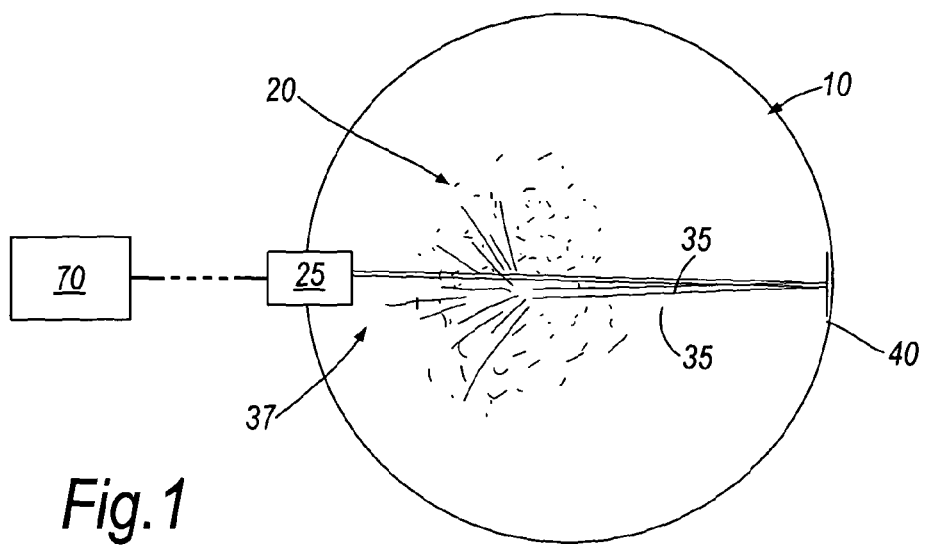
FIG. 1 shows a transverse cross-sectional view of a stack including an apparatus according to a first example embodiment of the invention.
Figure 2:
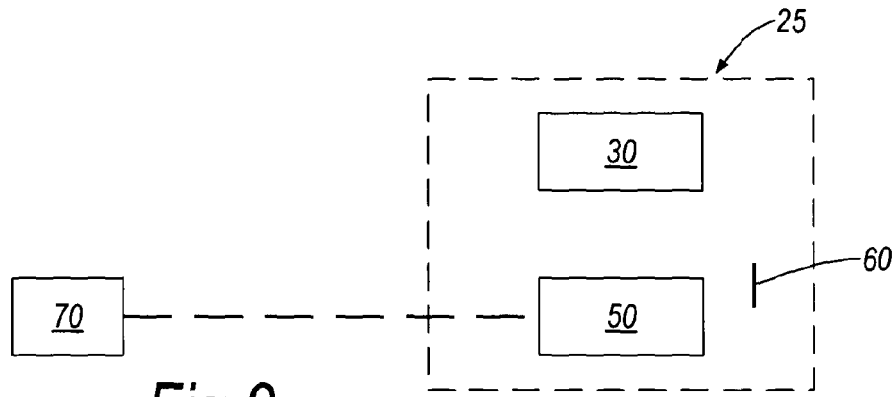
FIG. 2 shows schematically the apparatus of FIG. 1 in more detail.

In a first example embodiment of the invention, a stack 10 contains a flow of particles 20. In a wall of the stack 10, there is mounted a particle monitor housing 25. On the wall of the stack 10 opposite the housing 25 there is mounted a mirror 40. In this example embodiment, the mirror 40 is a plane mirror, but, in alternative embodiments, other forms of reflector may be used. The laser beam 35 is emitted from the housing 25 and reflected back towards the housing 25 by the mirror. The beam 35 is scattered from the particles 20 flowing in the stack 10. An image of the light 37 scattered from the particles 10 is obtained. The image is passed to the data processing apparatus 70.

The housing 25 contains a laser 30 and an imager 50. The laser beam 35 is emitted by the laser 30, and the scattered light 37 is imaged by the imager 50. The image of the scattered light 37 is passed to data processing apparatus 70 from the imager 50. In this example embodiment, light scattered from the reflector 40 or from any other region except that containing scattering particles is blocked from the obtained image by a physical mask 60.

The imager 50 has a field of view selected to be sufficiently small to get good spatial resolution in all three dimensions whilst being sufficiently large for all of the range (i.e. the width of the particle flow across the stack 10) to be in focus. The imager 50 is positioned and oriented to have a field of view (FIG. 3) that includes substantially all of the light 37 scattered from the particles 20. However, in order to achieve that, it will usually be the case that the imager 50 is also positioned and oriented to have a field of view that includes unwanted scattered light 140. That unwanted scattered light 140 would disrupt the accuracy of the measurement obtained via the imager 50 were it not blocked by the mask 60, which is shaped and positioned to block the unwanted scattered light 140 from the image 101 of light 37 scattered from the particles 20.

Figure 3:
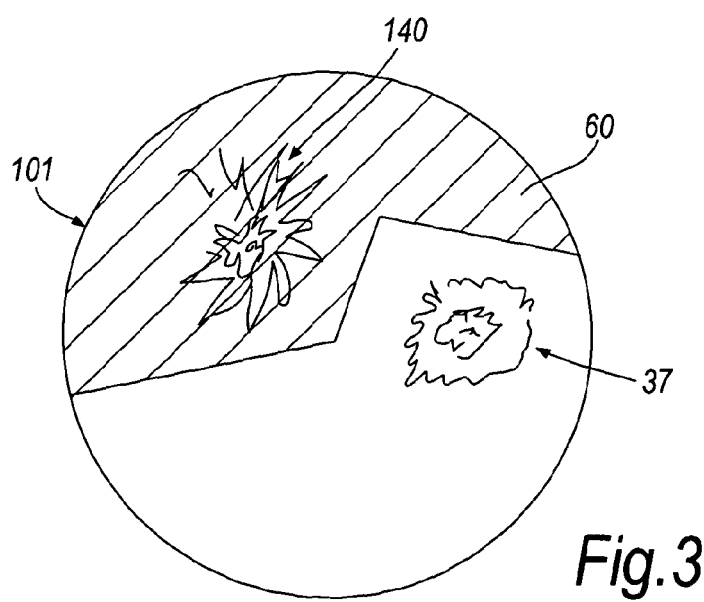
FIG. 3 shows an image representative of a typical image as would be obtained from the apparatus of FIGS. 1 and 2.

Note that in FIG. 3, the light 37 scattered from the particles 20 is spatially resolved, in that different parts of it within the plane of the image 101 originate from different regions of the particles 20 across the cross-section of the stack 10. More specifically, as the laser beam 35 passes obliquely through the particles 20 (or, equivalently, as the light 37 scattered from the particles 20 and imaged by the imager 50 is scattered at an angle), the light 37 scattered from the farther side of the particle flow from the imager 50 (i.e. light scattered from particles closest to the reflector 40) appears at one extremity of the imaged scattered light 37 in FIG. 3, whereas light 37 scattered from the nearer side of the particle flow (i.e. the light scattered from particles farthest from the reflector 40) appears at the opposite extremity of the imaged scattered light 37.

Figure 4A:
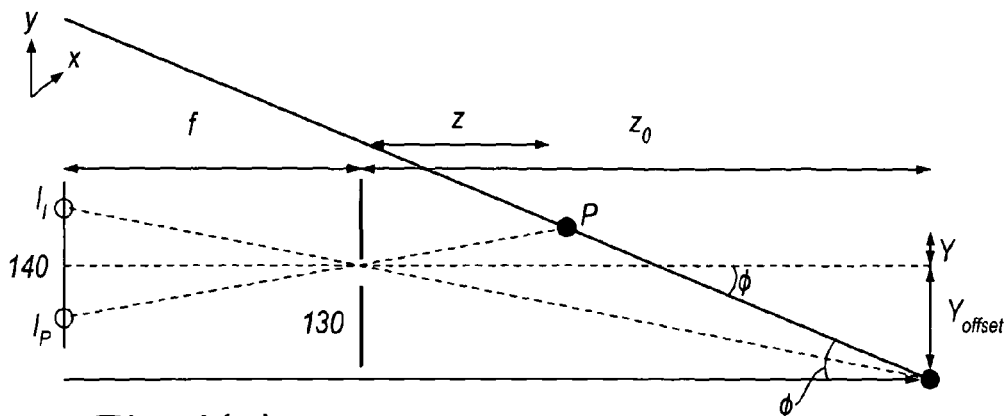
FIG. 4 shows (a) & (b) the geometry of an example apparatus according to an example embodiment of the invention, and (c) a 2-dimensional remapping of the beam onto an imager.
Figure 4B:
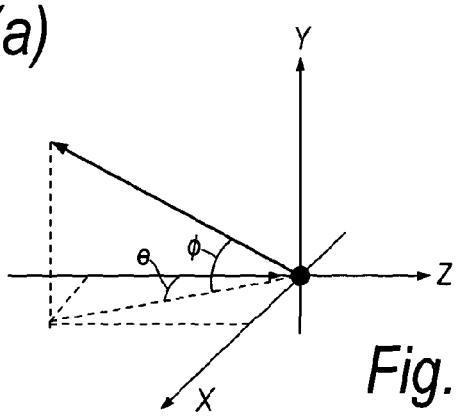

That is explained in greater detail in FIG. 4. When a laser beam travels in three dimensions through a scattering medium the (three-dimensional) scattered light detected by the imaging lens 130 and imager 140 is effectively remapped onto the two-dimensional imager. Range resolution and the quantification of scatter range is dependent on the angle of the beam in space, the extent of the scattering beam and the optical properties of the image-forming system. There are several ways of formulating the remapping of three dimensional space (X,Y,Z) to two dimensional space (x,y), and vice-versa, one of which is given here by way of example. With reference to FIGS. 4(a) and (b), point P is a generic point at (X,Y,Z) on a laser beam having a vector arranged at a horizontal angle of $\theta$ in the XZ plane and an angle $\phi$ defining the upwards or downwards direction of the beam. The starting point of the beam at the opposite side of the stack is given by the offset positions X.offset and Y.offset.

Any point P is defined as having an X co-ordinate given by $$X(Z,\theta,\phi) = X_{offset} + (Z_0 - Z) \cdot \tan(\theta)$$

And a Y co-ordinate given by $$Y(Z, \theta, \phi) := Y_{offset} + (Z_{,0} - Z) \cdot \frac{\tan(\phi)}{\cos(\theta)}$$

Remapping onto the detector array in xy is given by the co-ordinates $$x(Z, \theta, \phi) := -f \cdot \frac{X(Z, \theta, \phi)}{Z} + x_{offset}$$

and by $$y(Z, \theta, \phi) := -f \cdot \frac{X(Z, \theta, \phi)}{Z} + y_{offset}$$

Figure 4C:
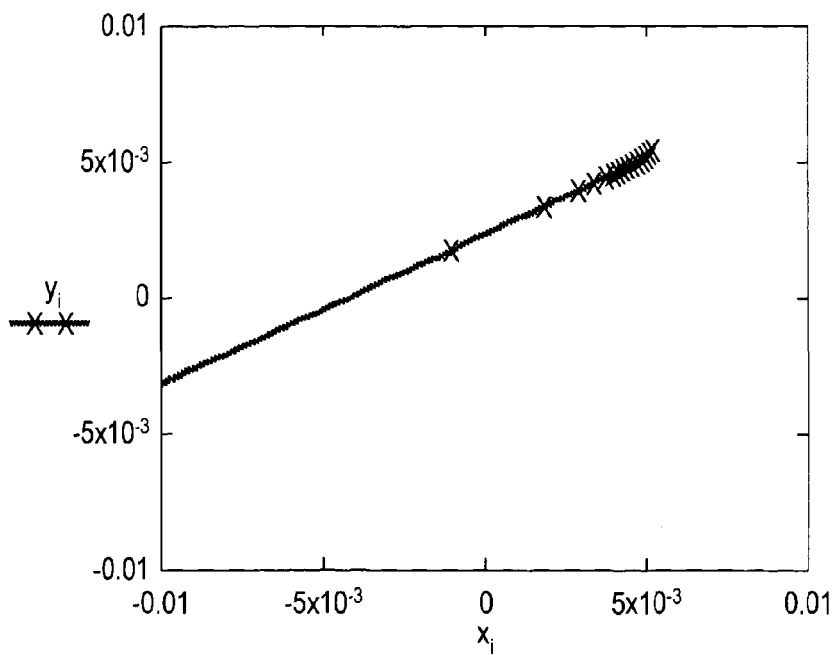

The resulting remapped beam has a typical appearance as in FIG. 4(c), which illustrates the non-linear relationship between the beam spacing and the imaged spacing, for equally spaced locations P along the beam. The calculation, therefore enables calculation of the range of any point of the beam, from a measurement on the image.

Figure 5:
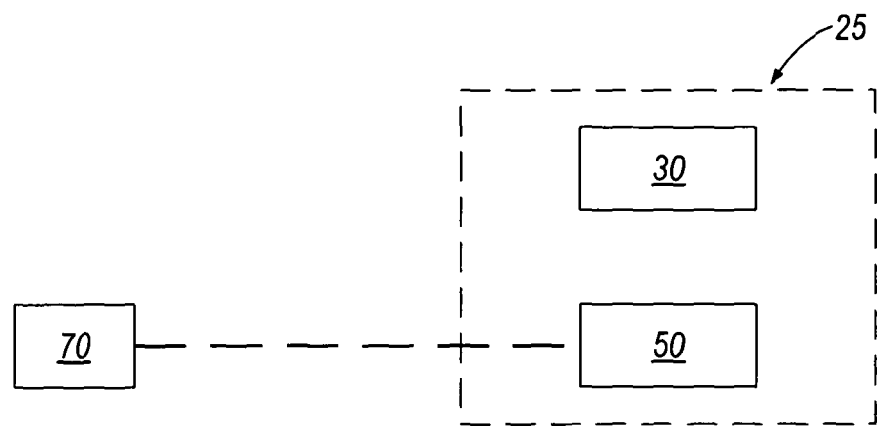
FIG. 5 shows schematically an alternative to the apparatus of FIG. 2, according to a second example embodiment of the invention.
Figure 6:
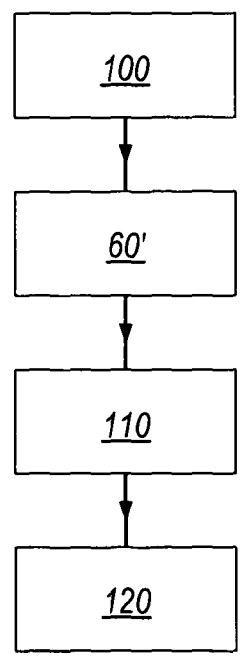
FIG. 6 shows data processing steps carried out in the apparatus of FIG. 5.

In an alternative, preferred, example embodiment (FIGS. 5 and 6), the filter 60 in the image 101 is embodied not as a physical mask (as it is in the first embodiment) but rather by applying a virtual mask in the data-processing apparatus 70. In the application of the virtual mask (FIG. 6), data 100 representing a raw image of the field of view of the imager 50 are received at the data processor 70. The unwanted scattered light 140 is blocked from the raw image data 100 by using a filter 60', in this example by taking a spatial Fourier transform of the raw image data 100 and then removing spatial frequencies known to correspond to unwanted scattered light 140, and then performing a spatial inverse Fourier transform to provide the image 101 without the unwanted scattered light 140. The spatial frequencies of the wanted and unwanted parts of the signal can be determined in a number of ways. An empirical approach would be to record a reference image, with no dust in the stack, and take its Fourier transform, which would then be deconvolved from measurement images which have "dust" in them, leaving the "dust only" signal. Another approach is to deliberately look for the pattern (in Fourier transform space) of the scattered light from a laser beam (i.e. pattern recognition in reciprocal space). A predictive approach would use knowledge of the size of an imaged "spot" due to a particle or group of particles, the inverse of which provides the spatial frequency of interest: the size distribution of such spots provides a spatial frequency bandwidth to be retained in the image upon which the inverse Fourier transform is carried out.

Further data processing 110 is then carried out in this example on the filtered image. In this example, the total intensity, integrated across the whole of the filtered image, is calculated and stored for each of a sequence of the filtered images and a temporal Fourier transform of the stored integrated intensities is calculated. The processed filtered image data are then analysed (in step 120) to provide information about the particles 20 in the stack 10: in this example, the quantity of particles 20 in the stack 10 is determined by observing the strength of the spectrum, obtained by the temporal Fourier transform, at frequencies known to correspond to scattering of light 37 from particles 20.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

In the second example embodiment described above, the virtual mask is applied in data-processing apparatus using software running on a processor, but in other, alternative example embodiments, the virtual mask is applied using dedicated electronic hardware filters.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A method of monitoring particles in a stack, the method comprising:
    generating on a first side of the stack a beam of light directed through the particles; and
    obtaining an image of light scattered from the particles by using an imager including a collecting lens through which the light scattered from the particles passes, wherein
    unwanted scattered light also passes through the collecting lens, and
    blocking from the image the unwanted scattered light that has passed through the collecting lens;
    wherein the beam of light is directed obliquely through the particles, so that different areas of the imager receive light scattered from particles at different ranges across the stack;
    and wherein the light scattered from the particles and passing through the collecting lens has been scattered in a direction that forms an angle of less than 30 degrees from the direction of the light beam as it passes through the particles.

2. A method as claimed in claim 1 in which the beam of light is generated on the first side of the stack and directed towards a second, opposite, side of the stack, the method further including the step of reflecting the beam back towards the first side of the stack and through the particles in the stack.

3. A method as claimed in claim 1, including one or more step selected from the following: summing the intensity of light in the entirety of the image; counting spots of light in the image; or identifying morphologically separated shapes for total area calculation.

4. A method as claimed in claim 1, in which the unwanted scattered light is blocked using a physical mask that prevents the unwanted scattered light from being imaged by the imager.

5. A method as claimed in claim 1, in which the unwanted scattered light is blocked from the image using a virtual mask, generated in hardware or software.

6. A method as claimed in claim 5, in which the image has an image space and the mask is applied in the image space or in a parameter space obtained by performing a spatial Fourier Transform on the image.

7. A method as claimed in claim 5, in which the virtual mask is applied by obtaining a sequence of the images and performing a Fourier Transform on the sequence of images in the time domain.

8. A method as claimed in claim 7, in which the images are processed before the Fourier Transform is applied.

9. A method as claimed in claim 8, in which the processing results in a sequence of data points from the sequence of images, and the Fourier Transform is performed on the resulting sequence of data points.

10. A method as claimed in claim 1, in which, in order to correct for background noise in the image, a reference field is determined.

11. A method as claimed in claim 1, including the step of monitoring, during monitoring of the particles in the stack, one or more areas of the image that is not illuminated by scattered light.

12. A method as claimed in claim 1, including the step of identifying the range from which each pixel of the imager detects scatter.

13. A method as claimed in claim 12, in which the range at which each pixel of the imager detects scatter is used to calibrate the intensity measured at each pixel of the imager and thereby to calculate the distribution of particles across the stack.

14. A method as claimed in claim 12, in which the range at which each pixel of the imager detects scatter is used to calibrate the intensity measured at each pixel of the imager and thereby to calculate a weighted average of particle distribution across the stack.

15. A method as claimed in claim 1, in which a range-resolved set of data points is obtained from the image by integrating over each row or each column of pixels in the imager to generate a single data point for each row or each column.

16. An apparatus for monitoring particles in a stack, the apparatus comprising:
   a light source for generating on a first side of the stack a beam of light directed through the particles in the stack;
   an imager for obtaining an image of light scattered from the particles, the imager including a collecting lens for collecting the light scattered from the particles; and
   a filter arranged to block from the image unwanted scattered light that has passed through the collecting lens into the imager;
   wherein the light source is arranged to direct the beam of light obliquely through the particles, so that different areas of the imager receive light scattered from particles at different ranges across the stack and the light scattered from the particles and passing through the collecting lens is scattered in a direction that forms an angle of less than 30 degrees from the direction of the light beam as it passes through the particles.

17. An apparatus as claimed in claim 16, including a reflector for mounting on a second, opposite side of the stack and for reflecting the beam back towards the first side of the stack.

18. An apparatus as claimed claim 17, in which the apparatus is arranged so that the imager is positioned between the direction of the light beam emitted from the light source and the direction of the light beam as it is reflected by the reflector.

19. An apparatus as claimed in claim 17, in which the light source and the imager are housed together in a common housing.

20. An apparatus as claimed claim 16, further comprising data processing means for carrying out one or more data processing steps.

21. An apparatus as claimed in claim 16, in which the filter is a physical mask.

22. An apparatus as claimed in claim 16, in which the filter is an electronic or software filter.

* * * * *